United States Patent [19]
Amos, Jr. et al.

[11] Patent Number: 6,159,177
[45] Date of Patent: Dec. 12, 2000

[54] DRAINAGE CATHETER ANCHOR LOCKING MECHANISMS

[75] Inventors: Raymond George Amos, Jr., Spencer; Boyd Allen Colvin, Indianapolis; Srinivas Nishtala; D. H. Perkins, both of Bloomington; Jefferey Carl Smith, Poland, all of Ind.

[73] Assignee: Scimed Life Systems, Maple Grove, Minn.

[21] Appl. No.: 08/940,406

[22] Filed: Sep. 30, 1997

[51] Int. Cl.[7] ................................................ A61M 37/00
[52] U.S. Cl. ............................................. 604/95; 604/164
[58] Field of Search .................................... 600/433–435, 600/585; 604/95, 104, 105, 106, 107, 108, 109, 523, 524, 528, 164, 174, 178

[56] References Cited

U.S. PATENT DOCUMENTS

| | | | |
|---|---|---|---|
| 4,586,923 | 5/1986 | Gould et al. | 604/95 |
| 4,643,720 | 2/1987 | Lanciano | 604/95 |
| 4,664,113 | 5/1987 | Frisbie et al. | |
| 4,740,195 | 4/1988 | Lanciano | 604/95 |
| 4,898,577 | 2/1990 | Badger et al. | 604/528 |
| 5,030,204 | 7/1991 | Badger et al. | 604/95 |
| 5,041,085 | 8/1991 | Osborne et al. | 604/171 |
| 5,185,004 | 2/1993 | Lashinski | 604/95 |
| 5,342,299 | 8/1994 | Snoke et al. | 604/95 |
| 5,419,764 | 5/1995 | Roll | 604/95 |
| 5,848,986 | 12/1998 | Lundquist et al. | 604/95 |

*Primary Examiner*—Glenn K. Dawson
*Assistant Examiner*—Catherine Serke
*Attorney, Agent, or Firm*—George A. Herbster; Pearson & Pearson

[57] ABSTRACT

A drainage catheter includes a tubular member with an anchor at a distal end and suture threads extending from the anchor to the proximal ends of the tubular member. A locking mechanism attaches to the proximal end of the tubular member and includes a body with an extension of the lumen. A displaceable body in the locking mechanism body attaches to the proximal end of the sutures to control the amount of slack or tension in the suture threads. An extension of that displaceable body lies externally of the locking mechanism body to enable the operation of the displaceable body without handling the suture threads.

7 Claims, 17 Drawing Sheets

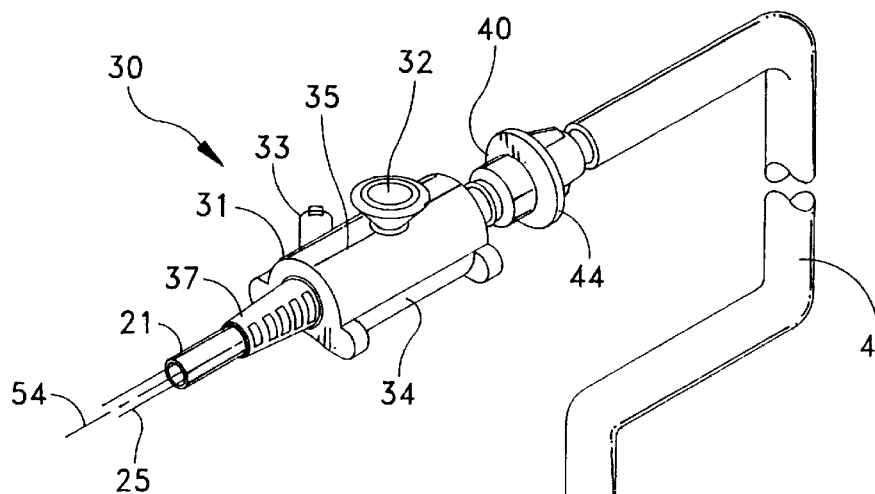
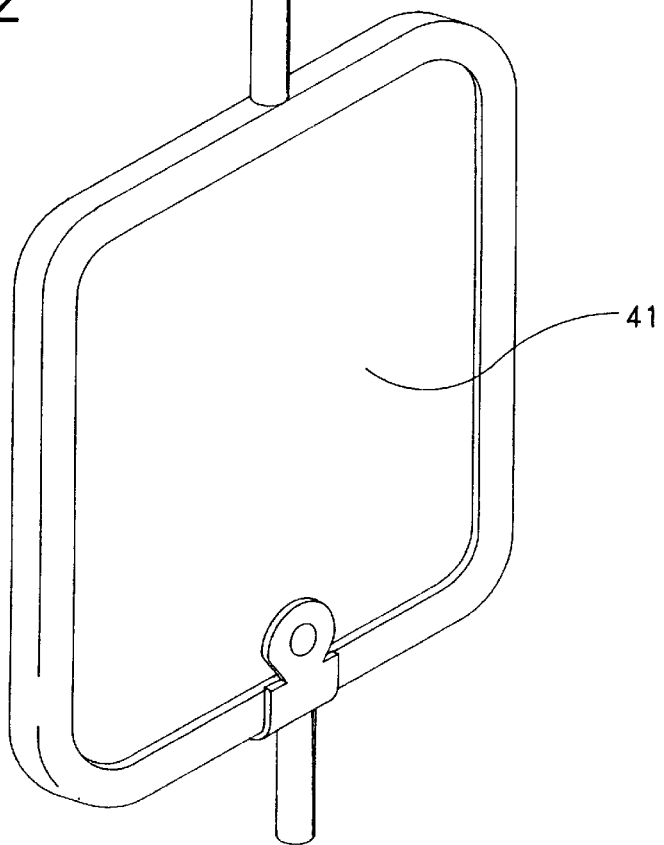
FIG. 2

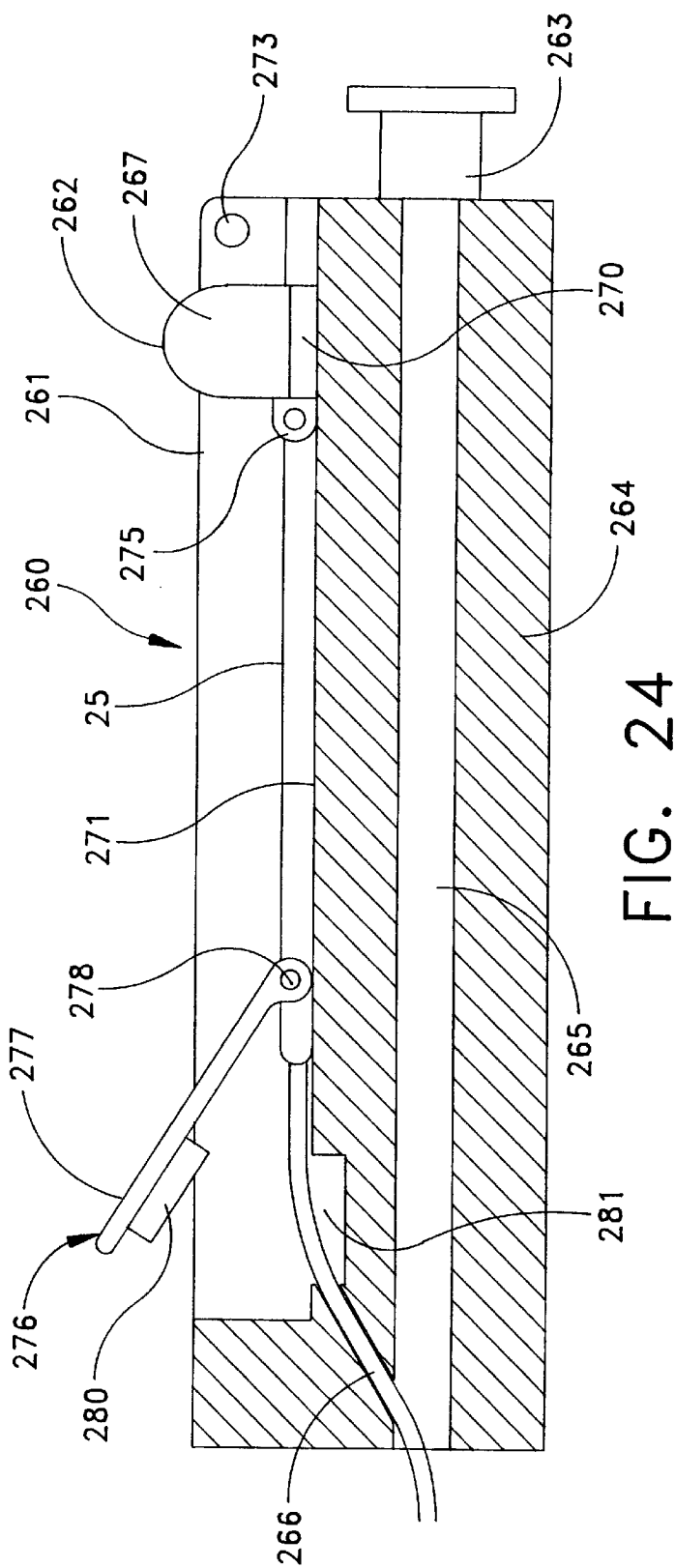
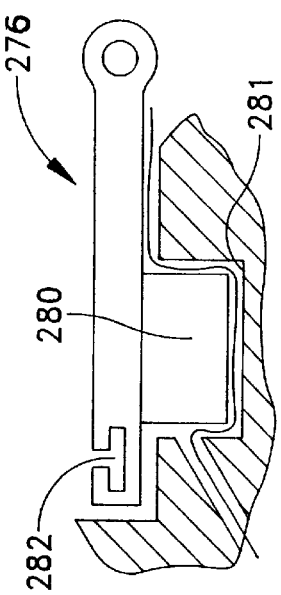
FIG. 24
FIG. 25

DRAINAGE CATHETER ANCHOR LOCKING MECHANISMS

BACKGROUND OF THE INVENTION

1. Field of the Invention

This invention generally relates to the field of catheters and more particularly to a catheter having a mechanism for retaining a distal end of the catheter in a predetermined configuration.

2. Description of Related Art

There are a variety of therapies or treatment modalities that require a catheter with a distal anchor or the like to retain the catheter in position. One particular application involves catheters used for drainage purposes. For example, procedures for the suprapubic catheterization of the bladder to drain the bladder after surgery or when the genitourinary system is plugged by an obstruction. Procedures using other percutaneously inserted catheters are also used to drain the kidney or biliary system as well as to drain abscesses, other sites of fluid collection and other viscera. Still other procedures use percutaneously inserted catheters as gastrostomy feeding tubes.

Generally these catheters are introduced into a patient through a large hypodermic needle or trocar. A guidewire is inserted through the needle or trocar which is then removed. The catheter tube, with a stiffening cannula, passes over the guidewire into the cavity. The cannula and guidewire can then be withdrawn leaving a portion of the catheter at its distal end in the desired cavity.

It is very easy to withdraw one of these catheters by movement of the body or under other conditions. Also these catheters generally have side ports at the distal end that can be inadvertently drawn into the abdominal cavity creating potential for severe infections when the catheter is inserted for bladder treatment.

Various catheters have been developed with diverse anchor structures to prevent inadvertent removal of the catheter from a patient. One such anchor is a "pigtail loop" formed by a flexible tube portion at the distal end of the catheter. The loops have a number of ports to ensure drainage. Generally the pigtail loop is preformed in the catheter because the flexible tube of the catheter is formed of a memory material. For introduction into a patient, a stiff cannula or similar implement is inserted through the catheter lumen to straighten the pigtail loop. The distal end of the flexible tube returns to the pigtail loop configuration after the cannula is removed.

Typically a suture thread extends through draw ports at two spaced positions along the distal portion of the flexible tube. These portions come into juxtaposition when the pigtail loop forms after the surgeon removes the cannula. Then the surgeon will take up any slack in the one or more suture threads that lead distally from the pigtail loop. When a suture thread is taut, it prevents the pigtail loop from straightening by holding the juxtaposed portions of the catheter together. Even taking up a portion of the slack can prevent complete straightening of the pigtail loop or other anchor.

When it is appropriate to remove the catheter, a cannula is inserted through the catheter from the proximal end until it encounters the pigtail loop. Then the suture threads are released and the stiff cannula can then be advanced to straighten the pigtail loop and facilitate the removal of the catheter from the patient.

With some catheters the proximal end of the suture thread is locked or retained in place by placing a hollow cap onto or over the proximal end of the catheter tube after the suture thread has been drawn into a taut condition. This structure traps the proximal end of the suture thread. Any protruding portion of the suture thread can then be cut if desired. Trapping or locking the suture thread prevents the pigtail loop from straightening.

With other catheters the suture thread is trapped between two or more hollow tubes one of which is slidably inserted axially into the other. A short length of suture thread generally is left hanging from the catheter so that if it becomes loose, it may be retightened. For example, U.S. Pat. No. 5,041,085 to Osborne et al. discloses a lockable sleeve drainage catheter with a flexible distal end that can form a pigtail loop. A locking sleeve positioned at the proximal end of the catheter draws the suture thread through a passageway to retain the distal end in the pigtail configuration. A locking collar at the proximal end of the elongated member tube has an annular recess formed therein. An annular step at the distal end of the lockable sleeve engages the recess to lock the sleeve in a fixed position. When fully extended and locked, the sleeve and elongated member form a fluid tight connection to prevent any leakage of fluids being drained.

U.S. Pat. Nos. 4,643,720 and 4,740,195 to Lanciano disclose alternative embodiments of a mechanism specifically designed for retaining the distal end of a catheter in a pigtail loop. As particularly shown in the later patent, a suture thread, as a flexible link, extends through a stop cock member that, when rotated, wraps the suture thread about the circumference thereof. Consequently after the distal end of the catheter forms the pigtail loop, rotating the member tensions the suture thread to prevent the pigtail loop from straightening.

U.S. Pat. No. 5,419,764 to Roll discloses still another structure that incorporates a twisting suture thread lock. The twisting lock is positioned at the proximal end of the catheter to draw the suture thread or flexible link through the passageway of the catheter after the distal end of the flexible tube forms the pigtail loop. Twisting the proximal member relative to the distal member of the twisting locking device causes the suture to wrap around a reel within the device. Once the locking mechanism tightens the suture thread and reaches its locked position, a rubber O-ring is compressed resulting in a fluid tight connection. The friction exerted between the O-ring and the adjacent members prevents unlocking of the system and unwinding of the suture thread.

Steerable catheters constitute another class of catheters that include deflectable tips that use suture threads as flexible links, but for steering purposes. Whereas in drainage catheters the anchors are preformed into a locking position so the locking mechanism merely takes up slack, steerable catheters use the suture threads or other flexible links for physically displacing the distal steering tip. For example, in U.S. Pat. No. 4,586,923 to Gould et al., one control mechanism at the proximal end of the catheter has a Y-shape, with one side of the "Y" being aligned with the catheter lumen. The other side of the "Y" receives a linearly or rotatably operated control mechanism for controlling the position of the flexible link and the distal tip.

U.S. Pat. No. 5,030,204 to Badger et al. discloses an axially displaceable manipulator that displaces a control line to deflect a distal tip and decrease the included angle between the distal portion and main portion of a shaft. Thus adjusting the control line position enables the catheter to steer the catheter by deflecting the catheter tip.

U.S. Pat. No. 5,185,004 to Lashinski discloses another mechanism including a translational nut mechanism for limiting the number of turns that can be applied to a steerable guidewire. Stops to proximal and distal motion of the nut provide the limit.

Each of the foregoing Lanciano, Osborne et al. and Roll references discloses a locking or retention mechanism for maintaining the pigtail of a drainage catheter in a locked or retention position. However, each has certain disadvantages. The Lanciano and Osborne et al. patents disclose mechanisms that can obstruct flow through the catheter. In the Osborne et al. and Roll patents it is often necessary to remove the locking mechanism from the patient's body in order to manipulate the locking mechanism. This can limit the possible locations for securing the locking mechanism. Moreover, the locking mechanism is typically attached to a patient by adhesive tape, so repeated manipulations and removals can cause patient skin irritation.

SUMMARY

Therefore it is an object of this invention to provide a locking mechanism for the tension member in a drainage catheter or the like that has a low profile, is compact and easy to use.

Another object of this invention is to provide a locking mechanism for a flexible tension member in a drainage catheter that minimizes flow obstructions.

In accordance with this invention a drainage catheter comprises a tubular member having a lumen therethrough and having a proximal end, a distal end, an anchor at the distal end and a flexible link extending from the anchor through the lumen to the proximal end. A locking mechanism at the proximal end for receives the flexible link and includes a locking mechanism body forming an internal cavity for connection to the tubular member whereby the cavity forms a passageway aligned along a cavity axis as a proximal extension of the lumen. A displaceable body in the locking mechanism body attached to the proximal end of the flexible link for controlling the slack of the flexible link in the lumen. An extension of the displaceable body exits the locking mechanism body for enabling the operation of the displaceable body from the exterior of the locking mechanism body.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIGS. 2 and 3 are views that depict one embodiment of this invention;

FIGS. 23 through 25 depict yet another additional embodiment of this invention.

DESCRIPTION OF ILLUSTRATIVE EMBODIMENTS

Figure 1:
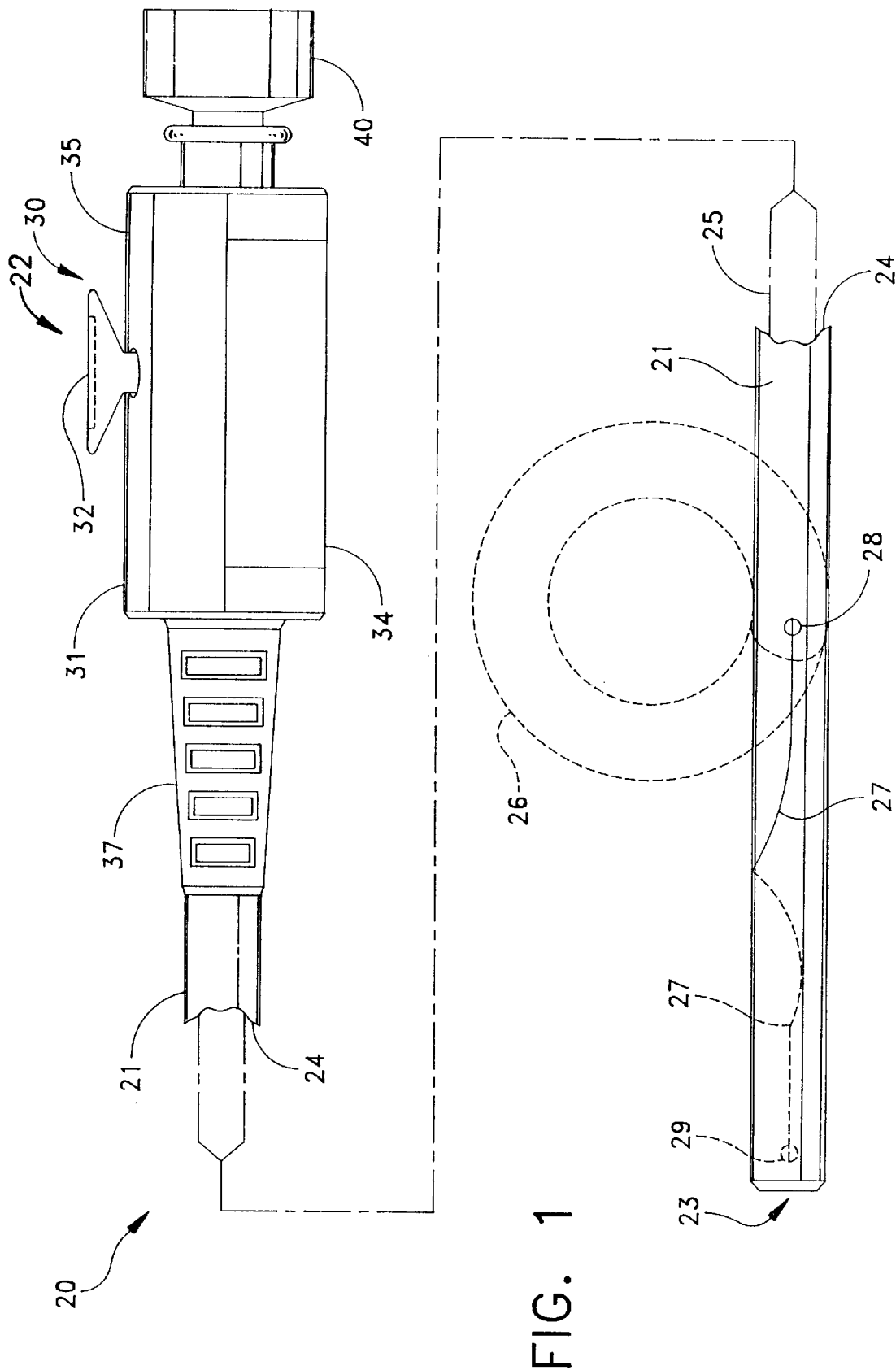
FIG. 1 is a perspective view of a catheter assembly constructed in accordance with this invention.

FIG. 1 depicts a catheter 20 with a radially flexible tube 21 that extends between a proximal end 22 and a distal end 23. A lumen 24 extends through the tube 21 and carries a flexible link 25 in the form of one or more suture threads. A two-part suture thread 25 is shown in FIG. 1. As shown by the solid lines in FIG. 1, the tube 21 extends along an axis when it is inserted and deflects into a pigtail loop 26 as shown by the dashed lines in FIG. 1 when a cannula or other straightening implement is removed from the lumen 24. As known, the pigtail loop 26 constitutes one form of an anchor.

A distal end portion 27 of the suture thread 25 extends through a draw port or aperture 28 displaced from the distal end 23 and a draw port 29 or other connection at the distal end 23. Typically a single suture thread has its mid point located at the distal draw port 29 with the resulting two strands or ports being led proximally through the lumen 24. A locking mechanism 30 constructed in accordance with this invention and located at the proximal end 22 attaches to the ends of the suture strands and includes a locking mechanism body 31 attached to the flexible tube 21 that carries a rotatable external control 32 and an integral leur connection 33.

When the pigtail loop 26 is straightened for insertion, the suture thread 25 pays out. If the cannula is withdrawn from the lumen 24 through the proximal end 22, the pigtail loop 26 forms such that the draw ports 28 and 29 are proximate each other leaving a portion of the suture, i.e., the portion 27, in a loose or slack form. Rotating the external control 32 then draws the strands of the suture thread 25 proximally until the slack introduced by the portion 27 between the draw ports 28 and 29 is eliminated. When the suture thread 25 is taut, it resists any forces that might otherwise tend to straighten the pigtail loop 26 because it locks the distal end 23, particularly the port 29, adjacent the port 28. To remove the catheter 20 in FIG. 1 a surgeon rotates the external control 32 in an opposite direction thereby to loosen the suture thread 25. Thereafter inserting the cannula through the lumen 24 from the proximal end 22 straightens the pigtail loop 26.

Figure 3:
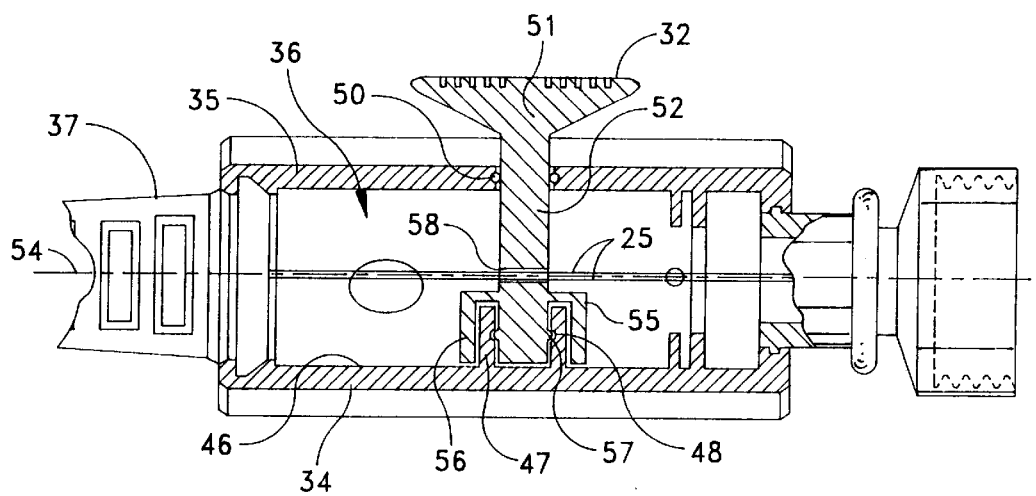

FIGS. 2 and 3 depict one embodiment of this invention that facilitates the manipulation of any slack in the suture threads 25 without obstructing flow. The locking mechanism 30 attaches to the proximal end of the flexible tube 21 and includes a locking mechanism body 31 and a displaceable body 32. In this particular embodiment the leur fitting 33 extends from the side of the locking mechanism body 31. The locking mechanism body 31 includes a base 34 and a cover 35 that define an internal chamber 36. At its distal end, the locking mechanism 30 includes a strain relief 37 at which point the flexible tube 21 attaches to the base 34.

At the proximal end, a proximal connector 40 provides a mechanism for connecting a drainage bag 41 through a tube 42. The drainage bag 41 may have a valve or connector 43 associated therewith. The tube 42 attaches to an end fitting 44.

The other end of the base 34 defines an internal chamber floor 46 from which extends a central hub 47 that includes a detent section 48. The cover 35 includes a sealed aperture defined by the cover structure including a circumferential O-ring groove 50.

The displaceable body 32 includes an actuator portion 51 that constitutes an extension of the displaceable body 32 that enables the operation of the displaceable body 32 from the exterior of the locking mechanism body 31. The displaceable body additionally includes a shaft 52 in the cavity 36 that lies transversely to a longitudinal axis 54 through the chamber 26. The shaft 52 terminates in an end portion 55 that includes an annular structure 56 with an internal detent 57 on an extension of the shaft 52. In accordance with one aspect of this invention, the locking mechanism body 31 is sized so that the chamber 36 has a cross-section relative to the axis 54 that is greater than the sum of the cross-sections of the flexible tube 21 plus portions of the displaceable body 32 and end shaft structure 55 lying within the cavity. This relationship enables fluid flow from the tube 21 through the locking mechanism without any obstruction.

The shaft 52 has a diametrically directed aperture 58 formed therethrough at some portion that is within the chamber 36. The suture threads 25 from the distal end of the catheter pass through this aperture 58 and can be tied or knotted. Consequently when the displaceable body 32 is rotated in one direction the suture threads 25 wind onto the shaft 52. When the displaceable body is then rotated on the reverse direction the suture threads pay off the shaft 52.

In this particular embodiment it is presumed that the friction of the detent mechanisms and sealing structures will prevent inadvertent rotation of the displaceable body 52. It will be apparent, however, that any of a number of different mechanisms could be incorporated to provide a positive lock that would prevent rotation. For example a mechanism could be added to this structure that would lock any rotation of the displaceable member in one longitudinal or transverse direction but would enable that rotation if the displaceable member 32 were displaced from that position, a so-called "push and rotate" mechanism.

Figure 4:
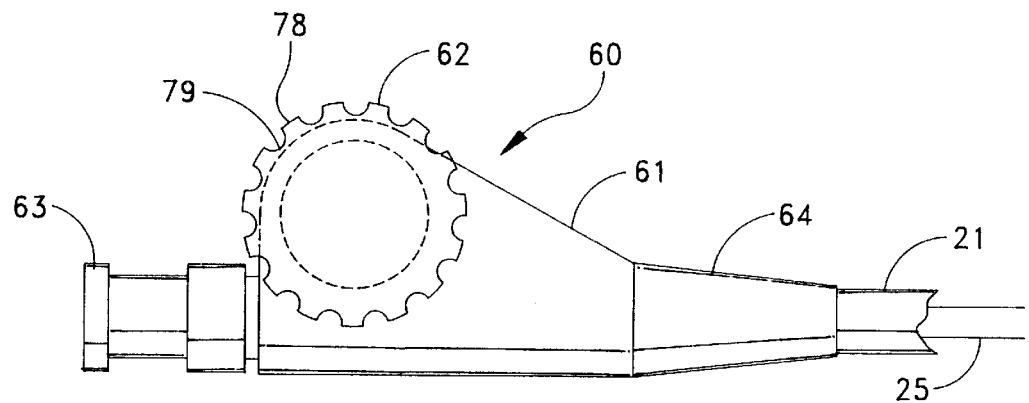
FIGS. 4 through 8 are views that depict another embodiment of this invention.

FIGS. 4 through 8 depict embodiments of this invention in which the displaceable body is offset from a lumen thereby to provide unobstructed flow through the locking mechanism. More specifically, FIG. 4 depicts a locking mechanism 60 with a locking mechanism body 61 and a displaceable member 62. At the proximal end the locking mechanism body 61 terminates in a leur fitting 63. At the distal end a strain relief 64 overlies the end of the flexible tube 21. As more clearly shown in FIG. 5, the locking mechanism body 61 includes a base portion 65 with a lumen 66 therethrough along a lumen axis 67. An extension 68 of the body defines a triangular portion terminating in an apex 69. A cross passage 70 traverses the extension 68 and an oblique passage 71 provides a path from the lumen 66 to the cross passage 70.

Figure 5:
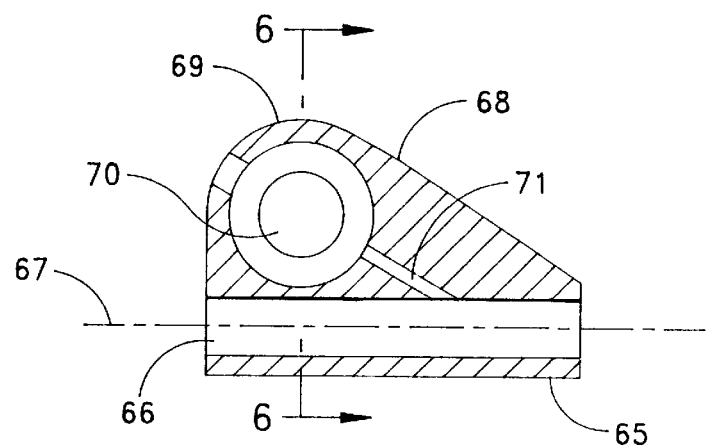
Figure 6:
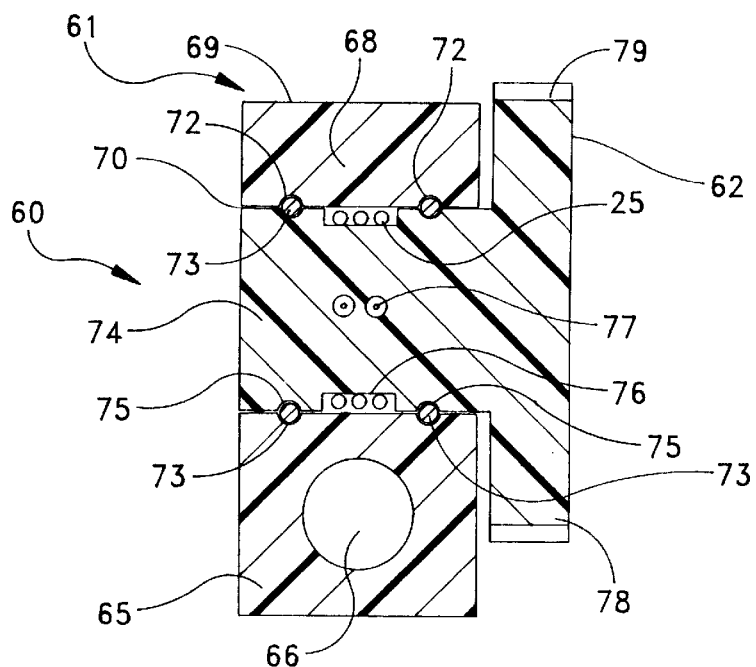

As more clearly shown in FIG. 6 that is a section taken along line 6—6 in FIG. 5, the extension 68 is also formed with spaced parallel circumferential grooves 72 that receive O-rings 73. A body portion 74 forms as an extension of the actuating portion of the displaceable member 62 is coextensive with the passage 70 and is formed with circumferential grooves 75 that register with the grooves 72. When assembled as shown in FIG. 6, the O-rings 73 act to seal the volume therebetween from the exterior of the locking mechanism body 61 and to provide a detent action that prevents the inadvertent removal of the displaceable member 62 from the locking mechanism body 61.

The shaft portion 74 can additionally include a circumferential channel 76 between the grooves 75 that provides a volume for wrapping the suture thread 25. One or more apertures 77 through the diameter of the shaft 74 can serve as anchor points for the proximal ends of the suture threads 25. Consequently, rotation of the displaceable member 62 in one direction wraps suture thread about the shaft 74 in the channel 76. Rotation in the opposite direction allows the suture thread to pay out.

Figure 7:
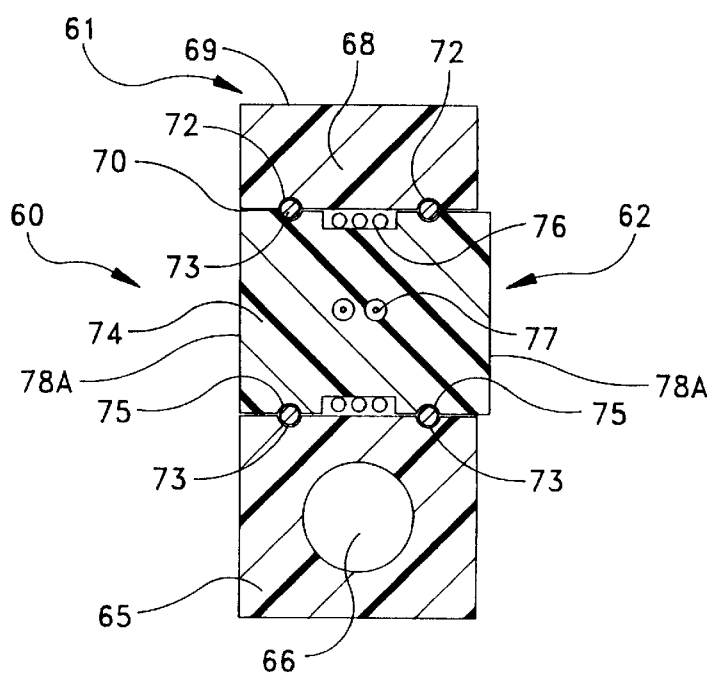
Figure 8:
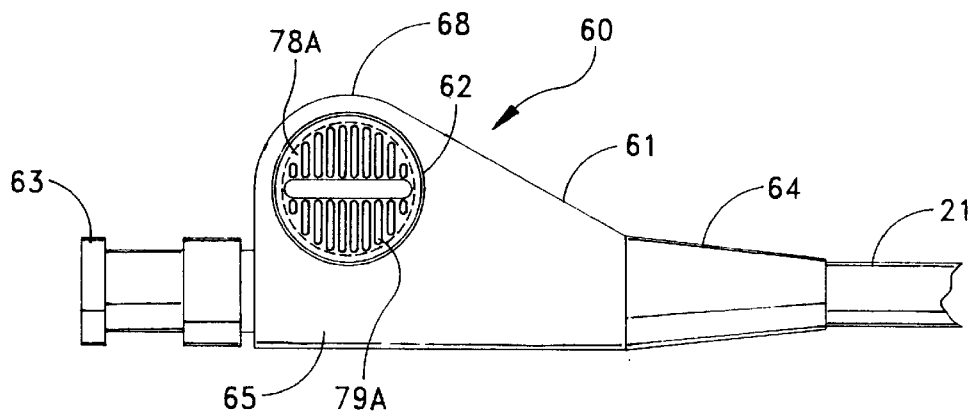

FIG. 6 depicts an actuator formed as an extension 78 of the displaceable shaft portion 74. In the particular embodiment of FIGS. 5 and 6, the actuator 78 has a knurled outer edge 79 to facilitate the manipulation or rotation of the displaceable member 62. FIGS. 7 and 8 depict an alternative embodiment in which the pads 78A are formed at each end of the shaft portion 74 to terminate proximate the side edges of the locking mechanism body 61. The surface 79A of one or both of the pads 78A can be treated by ridging or otherwise to facilitate rotation of the actuator 62.

Figure 9:
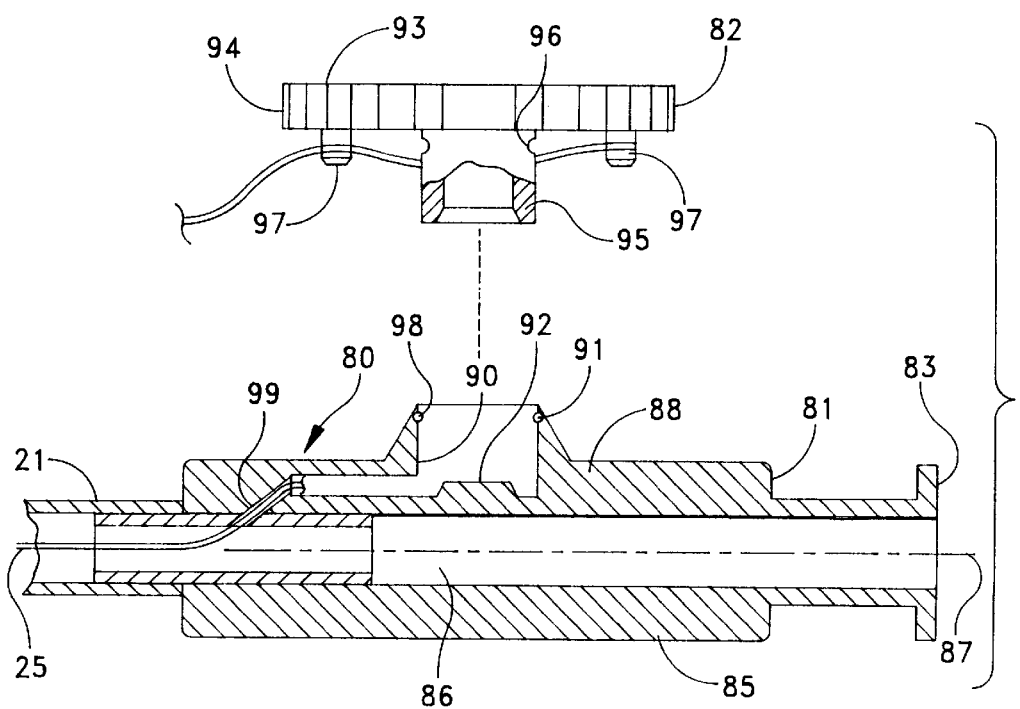
FIGS. 9 through 11 are views that depict yet another embodiment of this invention.
Figure 10:
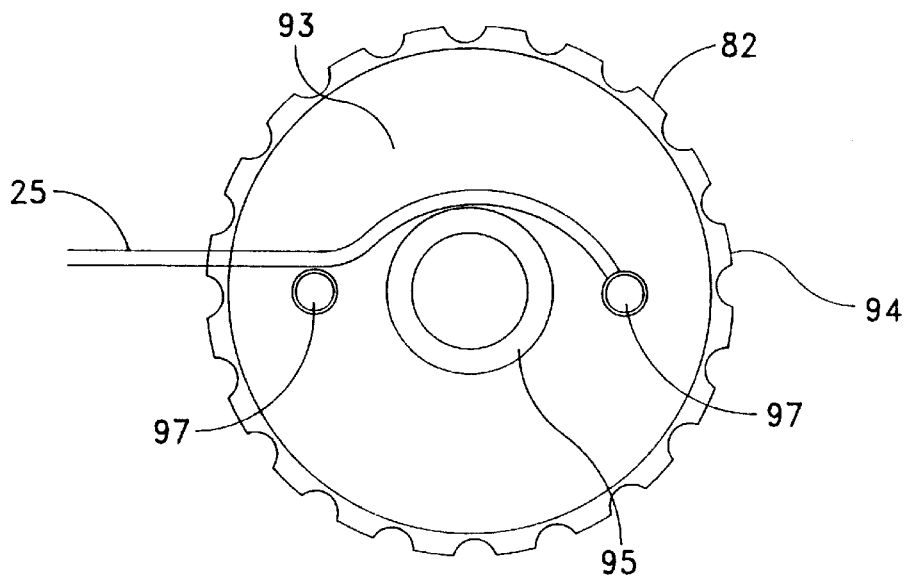

FIGS. 9 and 10 depict two variations on a third alternative embodiment of this invention in which a locking mechanism 80 attaches to a flexible tube 21 at its proximal end. The locking mechanism includes a locking mechanism body 81 and a displaceable body 82 that rotates within the locking mechanism body 81. At the proximal end the locking mechanism body 81 terminates in a leur fitting 83.

The locking mechanism body 81 includes a base portion 85 through which is formed a lumen 86. The lumen 86 can conform in size to the flexible tube 21 thereby to provide a substantially unobstructed flow through the locking mechanism 80. The lumen 86 extends along an axis 87.

In the orientation shown in FIG. 9, the locking mechanism body 81 additionally includes a support structure 88 formed above and separate from the lumen to define a cylindrical support well 90 with an O-ring groove 91 adjacent the outer lip thereof. A centering post 92 formed at the base of the support well centers a wheel structure that acts as the displaceable member 82. More specifically the displaceable member 82 includes a disk portion 93 with a knurled edge 94 for facilitating the manipulation of the displaceable member 82. A cylindrical structure 95 depends from the planar disk 93 to act as a bearing against the centering post 92. The structure 95 additionally contains an O-ring channel 96 proximate the planar disk 93. A pair of posts 97 also depend from the planar disk 93, are radially offset with respect to the bearing 95 and typically will be diametrically opposed as shown in FIG. 10. An O-ring 98 is captured between the O-ring grooves 91 and 96. Thus when the system is assembled, the displaceable structure 82 is free to rotate with respect to the locking mechanism body 81.

As the chamber formed by the surgical well 90 is separated from the lumen 86, the locking mechanism body 81 additionally includes a single passage 99 that communicates between the lumen 86 and the well 90. This passage allows the suture threads 25 to pass from the lumen 86 into the well 90 to be attached to one of the posts 97. As specifically shown in FIG. 10, clockwise rotation of the wheel 82 when viewed from the bottom wraps any slack suture thread 25 around the post 97. Counterclockwise or reverse rotation will allow the suture thread to pay out.

Figure 11:
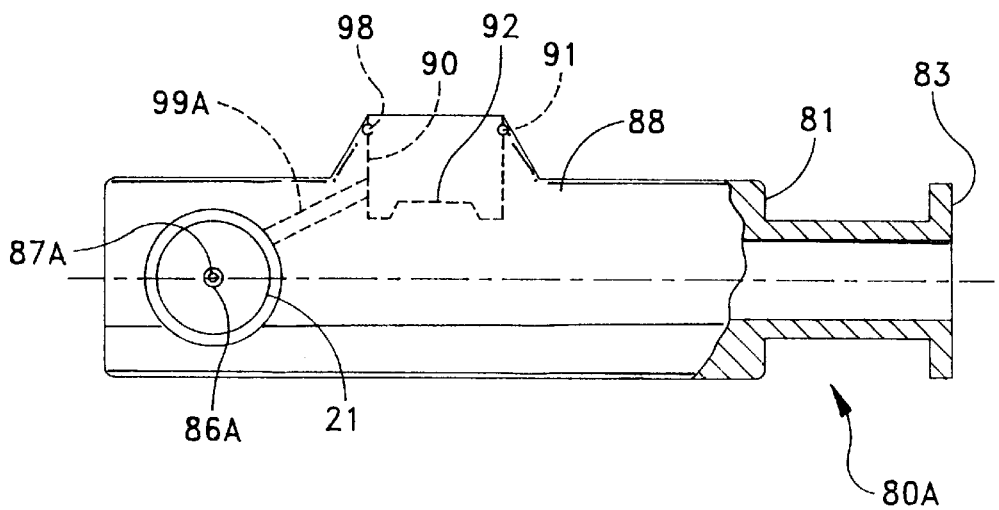

Whereas a central axis through the well 90 in FIG. 9 intersects the axis 87, the locking mechanism 80A shown in FIG. 11 includes a well 90 whose axis is transverse to but offset from an axis 87A through the lumen 86A. A passage 99A extends between the lumen 86A and the well 90. Thus when a displaceable body 82 such as previously described with respect to FIGS. 9 and 10 is inserted in the well 90 with the suture threads 25 attached, the locking mechanism again will enable rotation of the displaceable member 82 to take up any slack in the suture thread or pay out the suture thread 25 as required.

Figure 12:
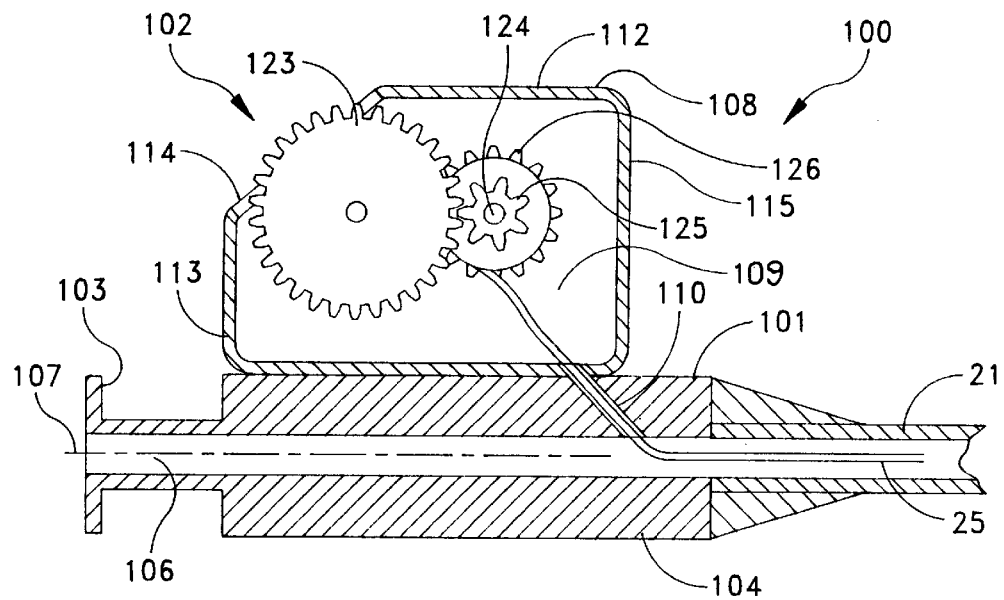
FIGS. 12 and 13 are views that depict still another embodiment of this invention.
Figure 13:
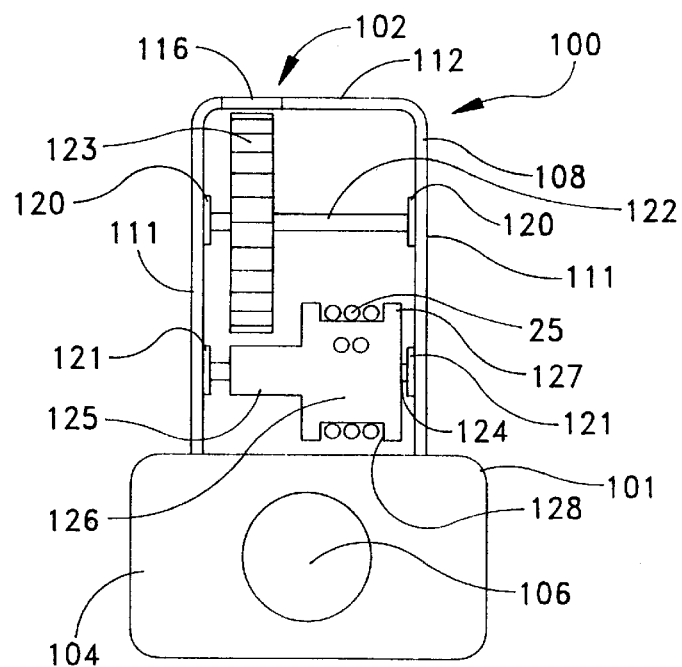

FIGS. 12 and 13 depict an alternative embodiment in which the mechanism for controlling the suture threads 25 includes a gear drive. More specifically, a locking mechanism 100 includes a body 101 and a displaceable mechanism 102 in the form of a gear drive. In the locking mechanism body 101 a leur fitting 103 extends from the proximal end of and receives the flexible tube 21 at the distal end of a base 104 that is formed with a through passage 106 that constitutes an extension of the lumen 24. Thus flow travels along a linear flow axis 107 that defines an unobstructed flow axis.

In this embodiment a housing 108 attaches to the base 104 to define another chamber 109. A passage 110 establishes a path between the lumen 106 and the chamber 109. The housing 108 comprises side walls 111, a top 112, a proximal end comprising a vertical wall 113, an oblique wall 114 and a proximal wall 115. As particularly shown in FIG. 13, the oblique wall 114 has formed an elongated slot 116.

The sidewalls 111 carry oppositely disposed bosses 120 and 121. The bosses 120 carry a shaft 122 and a drive gear 123. A segment of the gear edge extends through the slot 116 in the oblique wall 114 so a physician can manipulate the drive gear 123 by rotating it and the shaft 122 in the bosses 120. The bosses 121 carry a shaft 124 with a driven pinion 125 and connected drum 126. The pinion 125 engages the drive gear 123. Passages 127 through the drum 126 receive the proximal ends of the suture threads 25, so rotation of the drum 126 then wraps the suture threads in a channel 128.

In accordance with this embodiment of the invention, rotating the drive gear 123 provides a speed advantage, i.e., the mechanical advantage of the system is less than one. Although shown as a two-gear system, it will be apparent that a gear train including three or more gears could be substituted for the two-gear train to provide a further speed advantage. It is an object of this embodiment to provide a mechanism that would allow the physician to rotate the drive gear 123 through the exposed angle once and thereby wrap all slack in the suture threads onto the drum 126.

FIG. 12 discloses a passage 110 that is not in scale to facilitate an understanding of this invention. In actual practice the passage 110 diameter would be the minimum necessary to allow the suture threads to pass from the lumen 106 into the chamber 109 to thereby minimize leakage. It will also be apparent that the slot 116 could also be sealed to allow the drive gear 123 to rotate without any leakage from the chamber 109.

Figure 14:
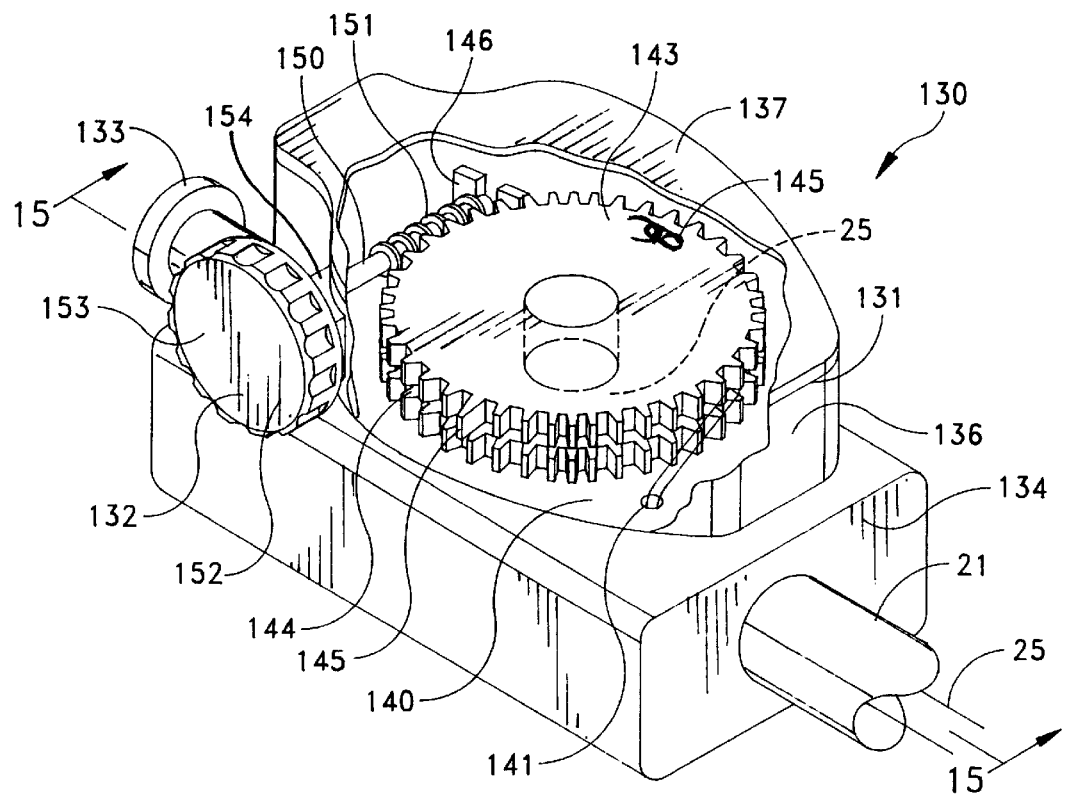
FIGS. 14 and 15 are views that depict yet still another embodiment of this invention.
Figure 15:
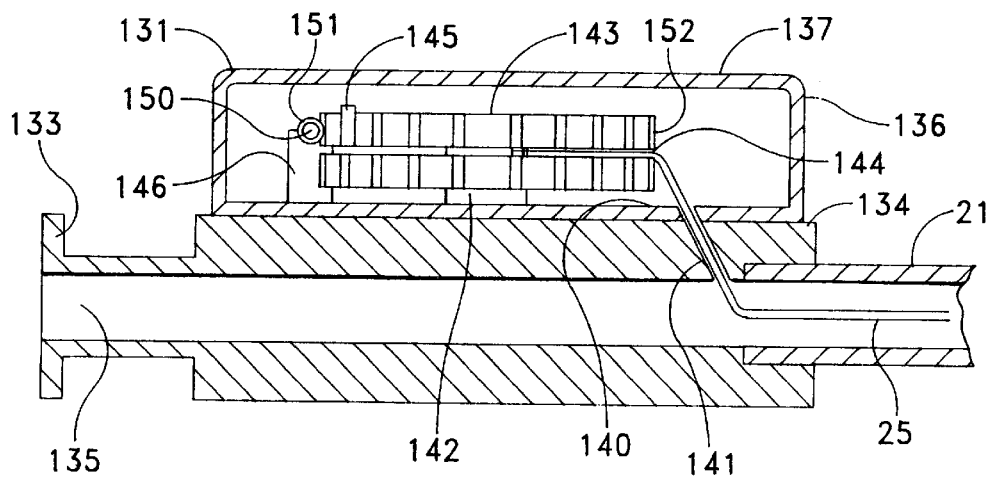

FIG. 14 and FIG. 15, that is a view taken along lines 15—15 in FIG. 4, depict another embodiment of this invention that utilizes a gear drive, but with a mechanical advantage that is greater than one. In this embodiment a locking mechanism 130 includes a locking body 131 and a displaceable member 132. A leur connector 133 extends from the proximal end of a base portion 134 of the locking body 131. A lumen 135 extends through the base portion 134 to provide an unobstructed flow path from the lumen in the flexible tube 21 to the leur connection 133. A housing 136 and cover 137 are attached to the base 134.

The housing 136 includes a floor 140 with a passage 141 that communicate through the lumen 135 to allow the suture threads to pass therethrough. The floor 140 also supports a hub 142 that carries a gear 143 for rotation about an axis that is vertical in FIG. 14 and intersects the lumen axis. The gear includes a center circumferential or peripheral channel 144 to which the proximal ends of the suture threads 25 are led. An axially extending passage 145 from the exterior or top surface of the gear 143 to the channel 144 and a similar passage from the channel 144 to the bottom surface provide tie points for the proximal ends of the suture threads. Rotation of the gear 143 about the hub then wraps or unwraps the suture threads from the gear, the suture threads lying in the channel 144.

Supports on opposite side walls of the housing 131, including a support 146 in FIG. 14, carry a shaft 150 and worm gear 151 that engages the external threads of the gear 143. A handle 152 with a knurled edge 153 attaches to the shaft 150 through a sealed port (not shown) to rotate the worm gear 151.

As will be apparent, the worm gear 151 and driven gear 143 produce a mechanical advantage greater than one and consequently a speed reduction. Thus a physician rotates the handle 152 through several rotations before the driven gear 143 rotates once. The driven gear 143 rotates in one direction or the other to remove slack from the suture threads 25 or allows the suture thread 25 to pay out. The mechanical advantage also prevents any tension on the suture threads from turning the drive gear as could occur if a pigtail loop, as an anchor, were to try to straighten.

In this particular embodiment, the housing 136 and cover 137 are sealed so the resulting chamber is sealed except for the port 154. Sealing of this port to prevent any inadvertent leakage from the housing is readily accomplished.

Whereas in FIGS. 2 through 15 the locking mechanisms are rotary devices, FIGS. 16 through 25 depict various embodiments that utilize linear motion to control the suture thread 25. In the particular embodiment of FIGS. 16 through 18, a locking mechanism 160 includes a locking mechanism body 161 and a displaceable member 162. The body 161 includes a leur connector 163 that extends from the proximal end of a base portion 164 to which the body 161 attaches. A lumen 165 extends through the base portion 164 to provide a linear unobstructed flow path between the leur connector 163 and the flexible tube 21.

Figure 17:
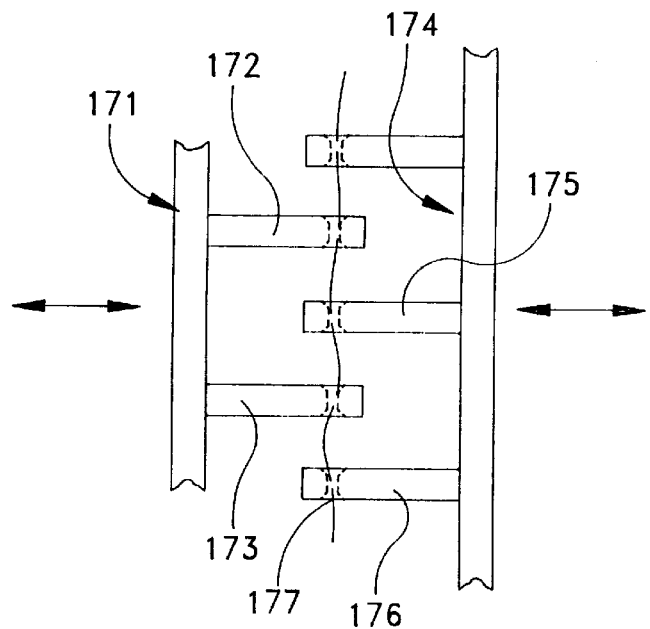
Figure 18:
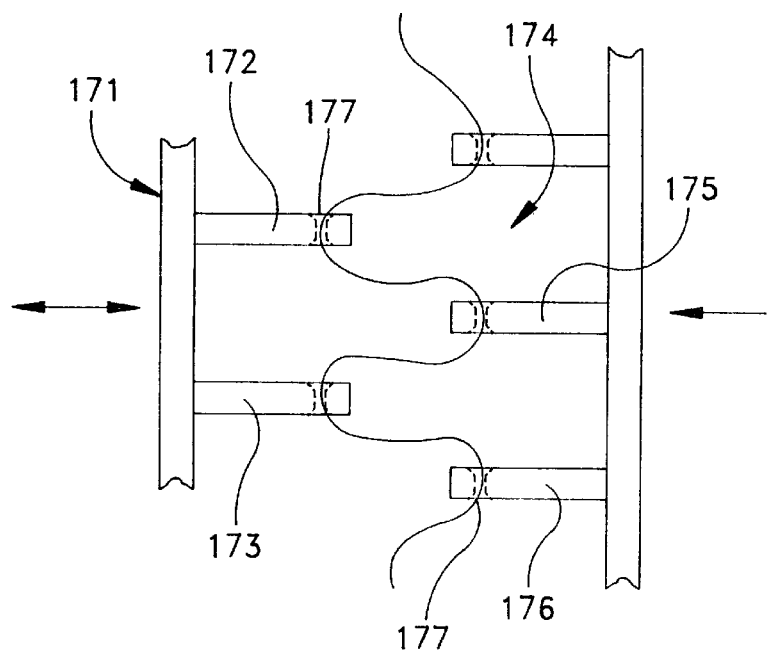

A housing 166 and cover 167 form a sealed chamber with a floor 170. The chamber carries a first finger set 171 that comprises a plurality of spaced fingers such as fingers 172 and 173 and a second finger set 174 that includes parallel spaced fingers 175 and 176. The fingers in the set 171 are parallel to but offset from the fingers in the set 174. FIGS. 17 and 18 depict the operation of this mechanism. In FIG. 17 the finger sets are positioned such that a suture passes through apertures 177 in each of the fingers in an essentially straight line. This would be the configuration of the finger sets 171 and 174 when the pigtail was straightened. When the pigtail forms, slack is taken up by displacing the finger sets 171 and 174 relative to and toward each other. As shown in FIG. 18, as this occurs the apertures 177 in adjacent fingers displace from each other laterally causing the suture thread to pass in a serpentine fashion through the fingers. Consequently the amount of slack taken up by translation will correspond to the total displacement of the fingers relative to each other and the number of fingers in the device. As will be apparent, some displacement would occur if the finger sets 171 and 174 were separated from the positions shown in FIG. 17.

Figure 16:
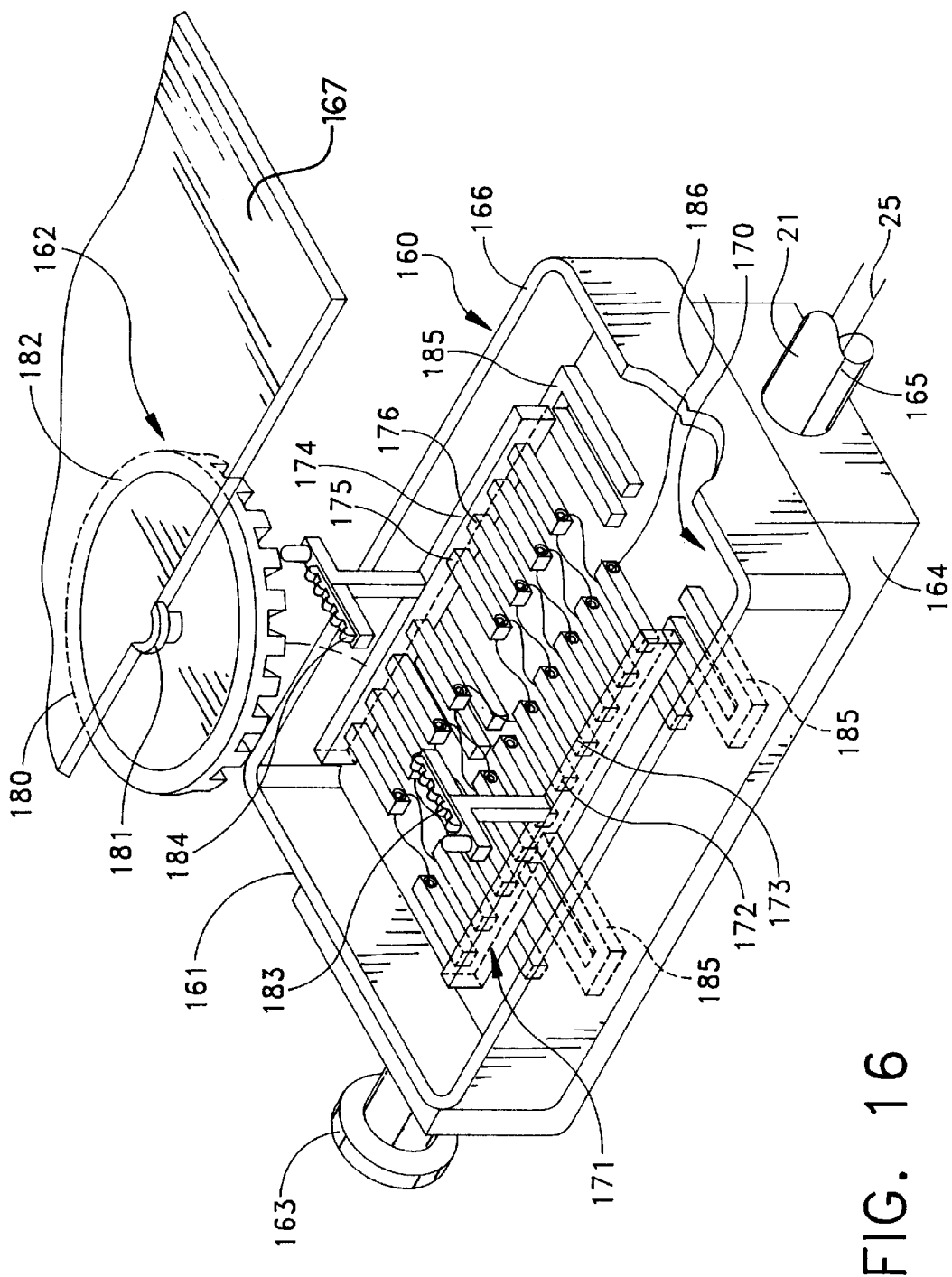
FIGS. 16 through 18 are views that depict still yet another embodiment of this invention.

In the particular embodiment of FIG. 16 an actuator in the form of an external knob 180 rotates a drive gear 182 through a sealing structure 181. In this particular example the gear 182 constitutes a rack-and-pinion system. More particularly the finger sets 171 and 174 include racks 183 and 184 respectively. In addition the finger sets slide are relative to each other, as shown in FIGS. 17 and 18, in slide supports 185. Consequently as a physician rotates the knob 180, the drive pinion 182 brings the two racks 183 and 184 together or moves them apart. As a result slack will be taken up or the suture thread will pay out depending upon the final position of the knob 180 and the finger sets 171 and 174. As will be apparent, the suture threads can pass to the lumen 165 through a passage 186 that extends between the lumen 165 and terminates at the floor 170.

Figure 19:
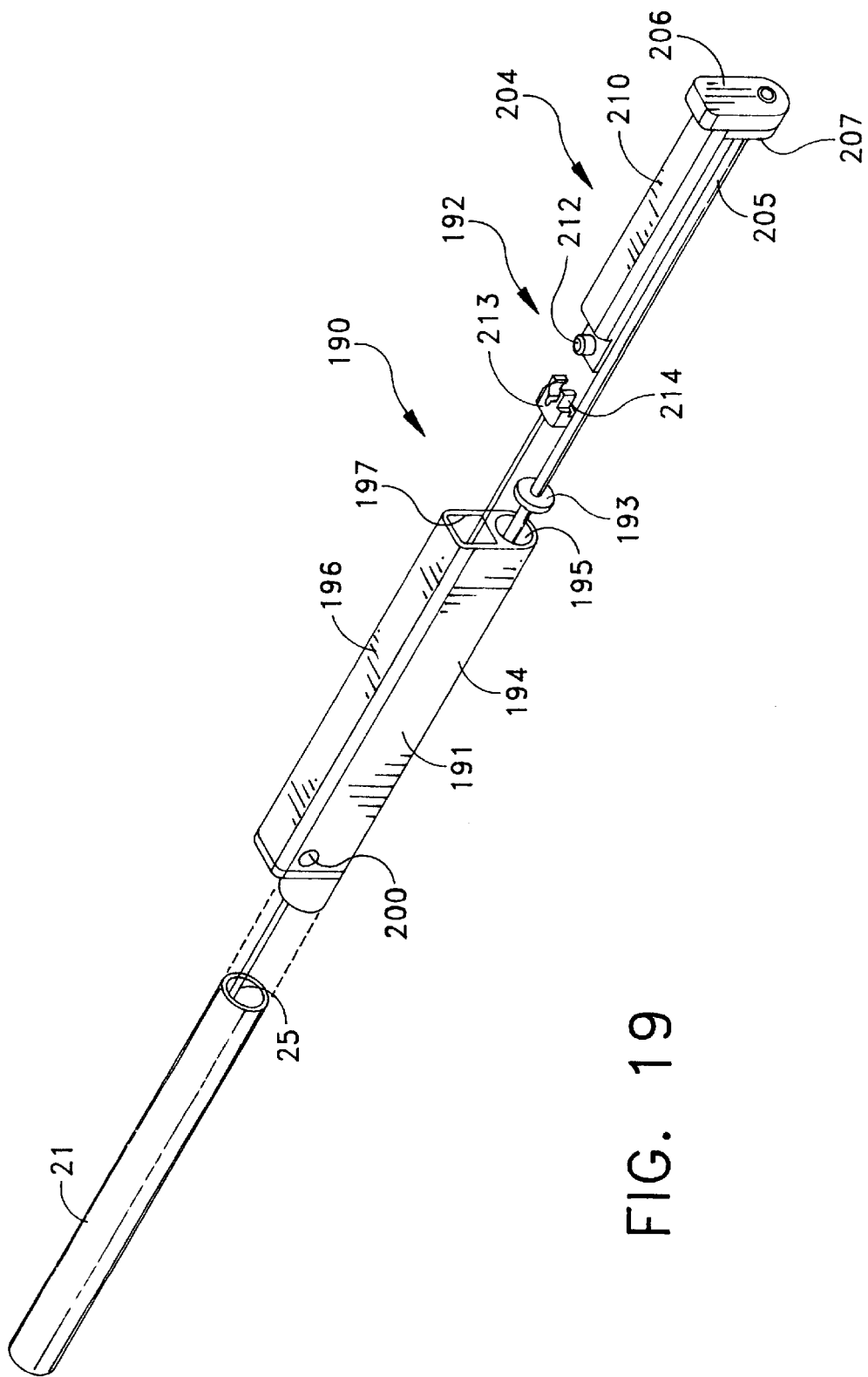
FIGS. 19 and 20 depict an additional embodiment of this invention.
Figure 20:
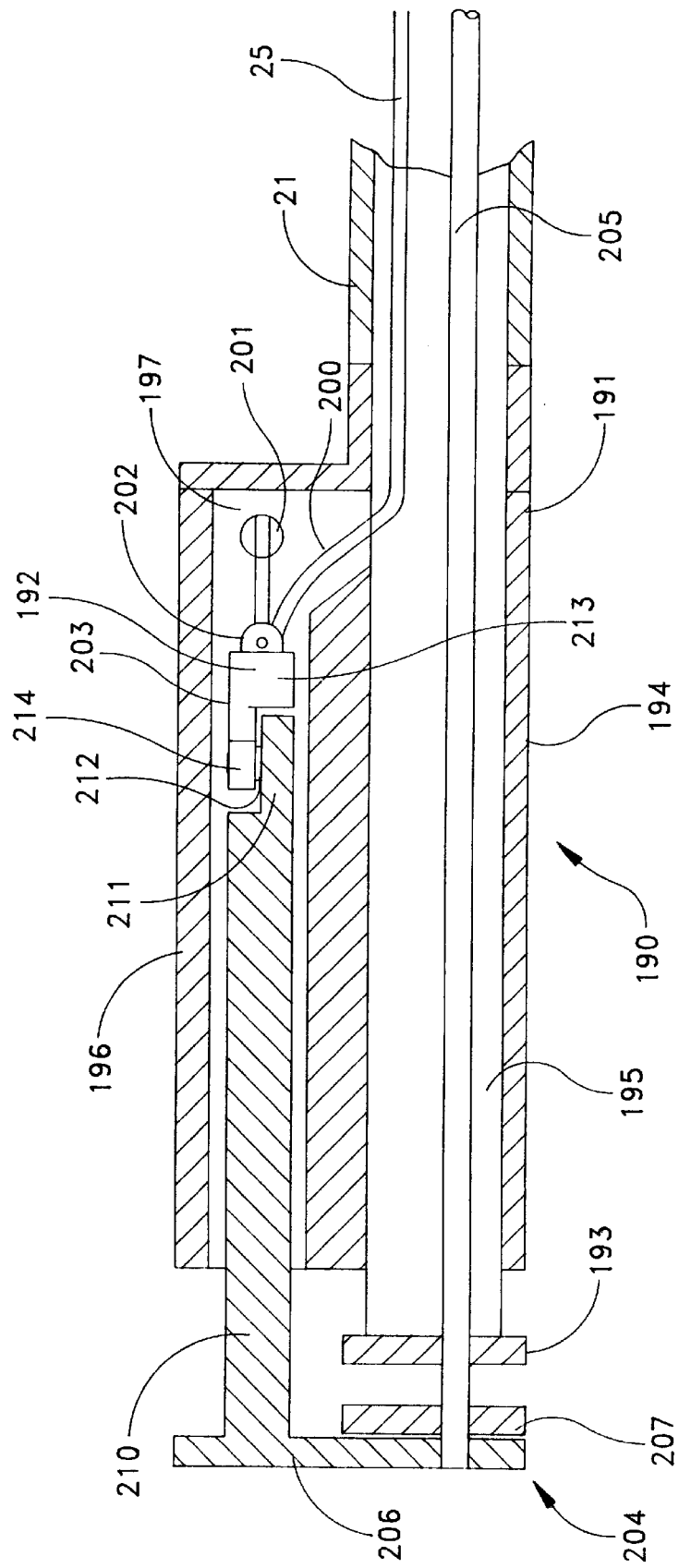

FIGS. 19 and 20 depict another embodiment of this invention that uses linear motion to control suture thread tension. As previously indicated, the drainage catheter is generally administered to a patient with a straightening cannula through the catheter lumen. FIGS. 19 and 20 depict an embodiment in which the straightening cannula additionally controls suture thread tension. More specifically, a locking mechanism 190 in this particular embodiment includes a body 191 attached to the flexible tube 21 and a displaceable member 192. A leur connection 193 at the proximal end of the body 191 enables the connection of a drainage tube and a lumen 195 extends through the body 194 to its distal end thereby to establish an extension of the lumen 24 and an unobstructed linear flow path. An upper housing 196 defines a longitudinally extending closed channel 197 parallel to the lumen 195.

A passage 200 extends between the lumen 195 and the longitudinal channel 197 with a closed proximal end. A pin or other similar device 201 provides a location for affixing the ends of one or more suture threads. The suture threads 25 then pass through a reeve port 202 on a carriage 203 that is adapted to slide longitudinally in the channel 197.

A straightening assembly includes a stiff cannula 205 that extends from a proximal end plate 206 that includes a leur connection 207 adapted to interconnect with the leur connection 193. An arm 210, parallel to and spaced from the cannula 205 extends distally from the proximal end plate 206 and terminates with a shelf 211 that carries a pin 212. The arm 210 and cannula 205 are offset such that the cannula passes through the lumen 195 while the arm 210 enters the channel 197.

The carriage 203 includes a body portion 213 sized to slide in the channel 197 and to carry the reeve port 202. At its proximal end the body portion 213 carries proximally extending spaced spring fingers 214 that are adapted to receive the pin 212 in a releasable connection.

Thus in accordance with this embodiment, a physician inserts the straightening cannula into the catheter. As the distal end of the stiffening cannula 205 reaches a pigtail, the pin 212 engages the fingers 214 and drives the carriage 213 to the distal end of the channel 197 thereby assuring that the pigtail can form, the channel corresponding in length to the total slack that is introduced into the suture threads when the pigtail forms. When the drainage catheter is properly located, the cannula is withdrawn. With this particular embodiment the physician withdraws the end plate 206. As this occurs, the pin 212 pulls the carriage 213 proximally to remove any slack from the suture threads 25 introduced as the pigtail forms. When the slack is removed, the carriage 203 will be at the proximal end of the channel 197. However, further displacement of the straightening assembly 204 will cause the fingers 214 to flex outward allowing the pin 212 to disengage and the cannula 205 to be withdrawn fully.

Figure 21:
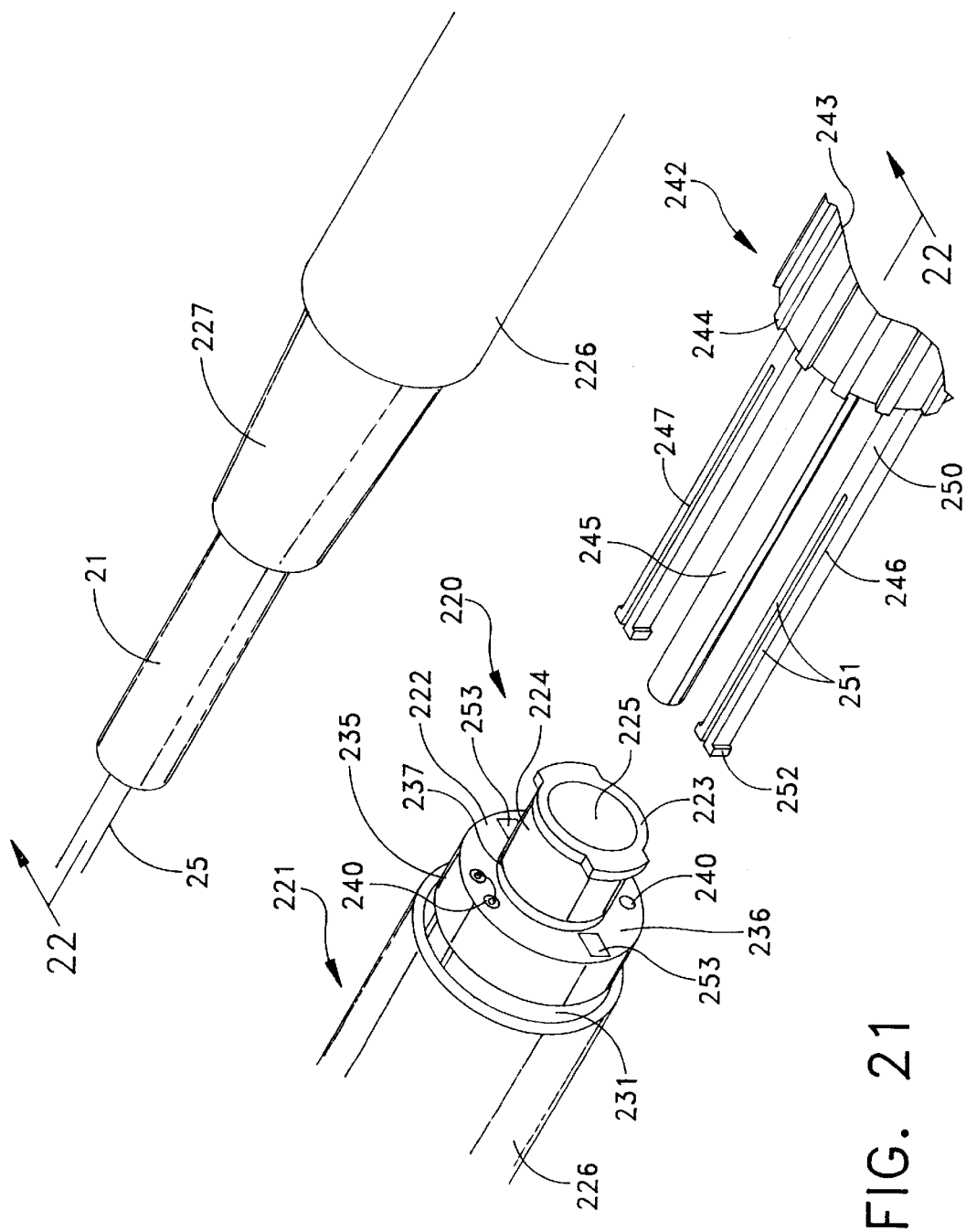
FIGS. 21 and 22 depict another additional embodiment of this invention.
Figure 22:
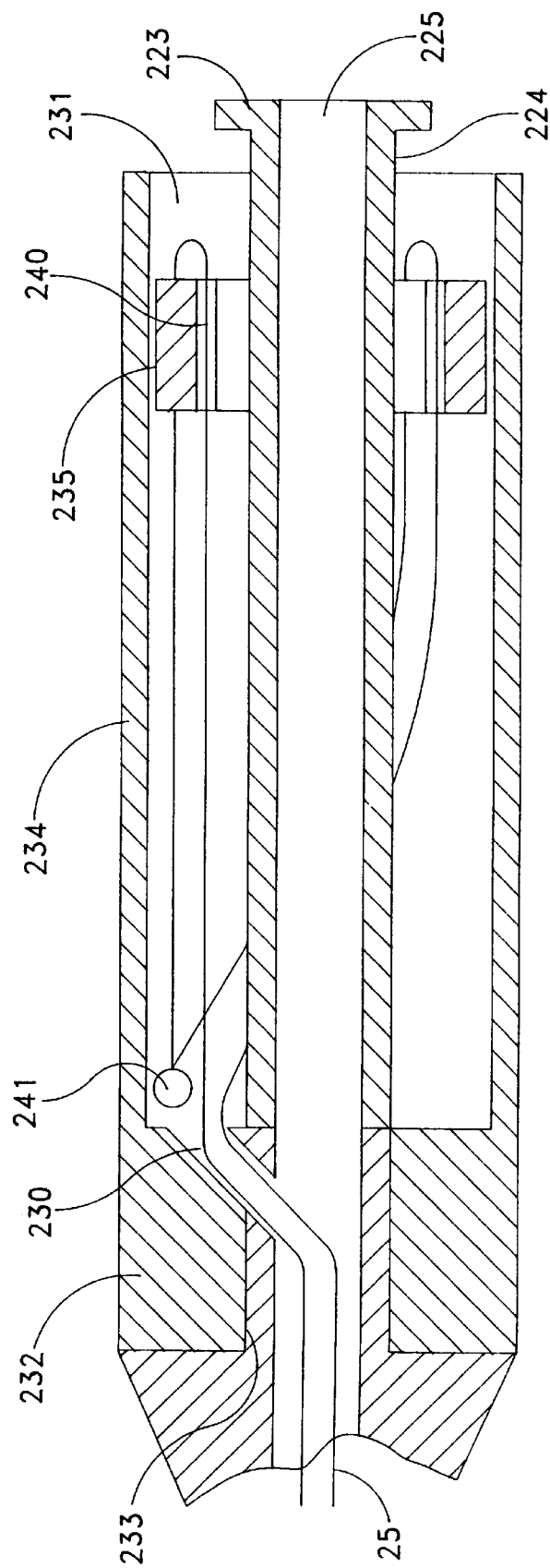

FIGS. 21 and 22, that is a view taken along lines 22—22 in FIG. 21, depict another embodiment of this invention that utilizes a cannula straightening assembly. In this embodiment a locking mechanism 220 includes a locking mechanism body 221 and displaceable member 222. A leur connector 223 at the proximal end of a body portion 224 defines a lumen 225 that provides an unobstructed linear flow path from the flexible tube 21 to the leur connector 223. The locking mechanism body 221 additionally includes an annular concentric outer body portion 226 that is coextensive with essentially all of the body portion 224. A strain relief 227 is shown as extending from the outer body portion 226.

A passage 230 through the body portion provides a path from the lumen 225 to a cylindrical chamber 231 intermediate the body portions 224 and 234. The chamber has closed distal and open proximal ends. The passage 230 is formed through the proximal base 232 that serves as a support from which the body portions 224 and 234 are cantilevered and further has a port 233 that receives the flexible tube 21.

An annular carriage 235 with an annular body 236 has a cross section that corresponds to the cross-section of the annular chamber 231 and includes a central aperture 237 that slides over the body portion 224. The annular carriage 235 additionally includes reeve ports 240 that allow the suture thread passing through the passage 230 to be lead through the reeve ports 240 back to a termination 241 at the distal end of the chamber 231. Thus motion of the carriage 235 in a proximal direction will take up any slack that might exist in the suture threads 25 with a 2:1 mechanical advantage.

In this particular embodiment a straightening cannula assembly 242 includes a handle 243 at the proximal end on a distal surface 244 that mates with the leur connector 223. A stiffening cannula 245 extends from the handle 243. A pair of finger assemblies 246 and 247 parallel and straddle the stiffening cannula 245. Each of the fingers 246 and 247 includes a base 250 attached to the distal end 244 of the handle 243 and distally extending spaced fingers 251 that have outwardly flared tips 252. When the spaced fingers 251 are compressed together, the tips 252 pass through axially extending passages 253 in the carriage 235.

As the stiffening cannula is inserted into the catheter, the fingers 246 and 247 pass through the apertures 253 in the carriage 235. As the pigtail straightens displacing any slack in the suture threads distally, the carriage 235 eventually rides to the distal ends of the fingers 246 and 247. As the physician subsequently withdraws the stiffening cannula assembly 242, the tips 252 eventually engage the annular carriage 235 and withdraw the carriage 235 proximally to the position shown in FIG. 21. At this point the physician can compress the fingers 251 thereby to release the straightening cannula assembly 242 from the carriage 235. In this particular embodiment is assumed that the friction between the outer annular surface of the carriage 235 and the inner surface of the annular body 226 provides sufficient friction to prevent accidental displacement of the carriage 235 in a distal direction that would otherwise unlock the pigtail loop.

Figure 23:
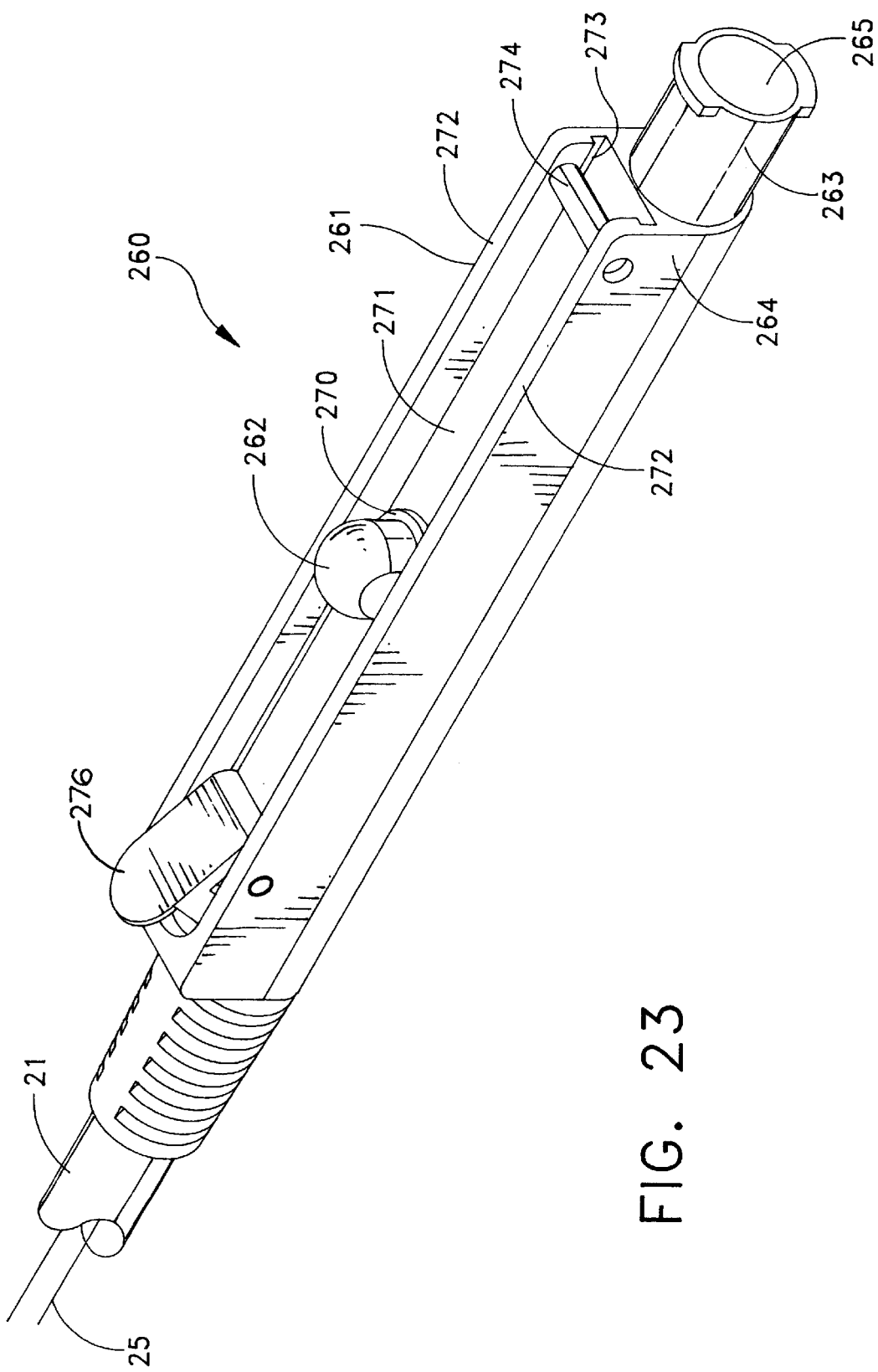

FIGS. 23 through 25 depict another embodiment of this invention that utilizes linear motion to the suture threads. In this particular embodiment a locking mechanism 260 includes a locking mechanism body 261 and displaceable member 262. A leur connection 263 extends from the proximal end of a body 264 and defines a lumen 265 that provides an unobstructed linear flow path from the flexible tube 21. A passage 266 provides a path for the suture threads 25 from the lumen 265 to a finger pad 267.

The finger pad lies on a slide 270 that rides in a channel formed by a floor 271, parallel sidewalls 272 and side channels 273. When it is desired to remove slack from the suture threads, a physician uses a finger to engage the finger pad 267 and displace the member 262 proximally to a stop position shown in FIG. 24 and defined by a transverse pin 274. In this particular embodiment a proximally extending pad 275 provides a means for attaching the proximal ends of the suture thread 25.

At the proximal end of the locking mechanism 260 a lever assembly 276 is formed with a plate 277 to rotate about a pivot pin 278. The plate 277 additionally carries a pad 280 that is preferably formed of a somewhat resilient material and that is aligned radially with a transverse channel 281 in the floor 271. As will be most apparent from FIG. 24, the passage 266 exits in a wall of the channel 281 so the suture threads 25 pass across the channel 281. The physician, after removing the slack from the suture threads 25, depresses the proximal lever assembly 276 thereby forcing the pad 280 into the channel 281. This seals the passage 266 and prevents inadvertent straightening of the pigtail.

As shown particularly in the detail of FIG. 25 the end of the plate can include a keyway 282 that would allow a physician to use a removable key to pivot the plate assembly 276 in a clockwise direction shown in FIG. 25 thereby to remove the pad 280 from the channel 281.

Figure 26:
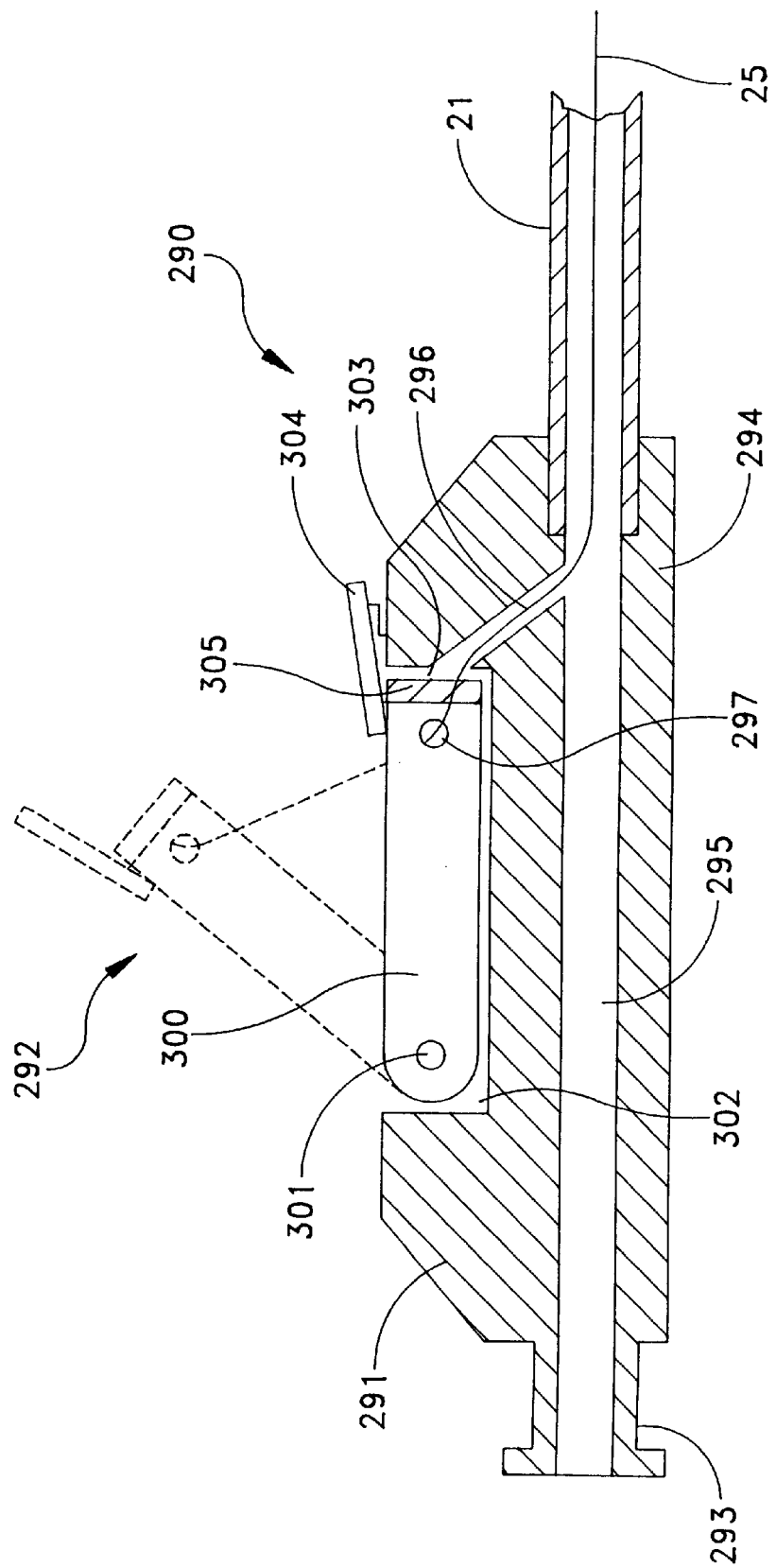
FIG. 26 depicts yet still another additional embodiment of this invention.

In the embodiment of FIG. 26 a locking mechanism 290 includes a locking mechanism body 291 and displaceable member 292. A leur connection 293 extends from the proximal end of a body 294 and defines a lumen 295 that provides an unobstructed linear flow path from the flexible tube 21. A passage 296 provides a path for the suture threads 25 from the lumen 295 to a tie point or aperture 297 formed in the displaceable member 292.

The displaceable member includes a lever 300 that rotates about a pivot 301 at the proximal end of the locking mechanism body 291. The pivot 301 lies in a well 302. The passage 296 exits the body 291 at the well through a distal wall 303. The distal end of the lever 300 carries a finger grip 304 that overlies a portion of the locking mechanism body when the lever 300 is closed, as shown by the solid lines in FIG. 26. A sealing pad 305 can be disposed at the distal end of the lever 300 to prevent leakage when the lever 300 is in the closed position.

In use, a physician allows the anchor, such as the pigtail loop 26 in FIG. 1, to form. Then the physician uses the finger pad 304 to raise the distal end of the lever to the position shown by the dashed lines to take up any slack in the suture thread. Then the physician returns the lever 300 to the well 302. As this occurs, the suture thread 25 that has been extracted through the passage 296 drops into the well 302 and is covered by the lever 300. When the lever 300 is closed fully, the sealing pad 305 seals the passage and prevents leakage from the passage 296.

Thus in accordance with the various embodiments of this invention, a drainage catheter includes a tubular member that has a lumen therethrough and that has a locking mechanism located at a proximal end thereof. The locking mechanism includes a locking mechanism body that forms an internal cavity or chamber along an axis as a proximal extension of the lumen. A displaceable body in the locking mechanism, that, in accordance with the various aspects of this invention takes on different forms, attaches to the proximal end of the flexible link or suture thread or threads for controlling slack therein. In each embodiment an extension of the displaceable body lies outside the locking mechanism for enabling the operation of the displaceable body from the exterior thereof. As will be apparent, there are a wide variety of specific implementations as depicted by the various embodiments. In addition many of the embodiments depict mechanisms that rely on friction to retain the suture threads in a locked mode. It will be apparent that a variety of different external locking mechanisms can be added to the structures in order to provide a positive locking function that prevents unwrapping of the suture threads.

This invention has been disclosed in terms of certain embodiments. It will be apparent that many modifications can be made to the disclosed apparatus without departing from the invention. Therefore, it is the intent of the appended claims to cover all such variations and modifications as come within the true spirit and scope of this invention.

What is claimed as new and desired to be secured by letters patent of the united states is:

1. A drainage catheter comprising:
   A) a tubular member having a drainage lumen therethrough and having a proximal end, a distal end, an anchor at the distal end and a flexible link extending from the anchor through said drainage lumen to the proximal end, and
   B) a locking mechanism attached to the proximal end for receiving said flexible link, said locking mechanism including:
      i) a locking mechanism body for connection to said tubular member as a proximal extension of said drainage lumen, said locking mechanism body forming an internal cavity extending along a cavity axis,
      ii) a displaceable body in said locking mechanism body and attached to a proximal end of the flexible link for minimizing the flexible link in said drainage lumen,
      iii) an extension of said displaceable body exiting said locking mechanism body in a sealed relationship with respect to said internal cavity for enabling the operation of said displaceable body from the exterior of said locking mechanism body.

2. The drainage catheter as recited in claim 1 wherein said displaceable body includes means for undergoing linear motion relative to said locking mechanism body.

3. The drainage catheter as recited in claim 2 wherein internal said cavity is separate from said drainage lumen and said locking mechanism body additionally includes an interconnecting passage therebetween.

4. The drainage catheter as recited in claim 3 wherein internal said cavity and said drainage lumen lie along parallel axes.

5. A drainage catheter as recited in claim 4 wherein said displaceable body includes a carriage for undergoing reciprocating motion within said cavity.

6. The drainage catheter as recited in claim 5 additionally comprising a straightening cannula assembly including:
   i) a straightening cannula for being inserted into said lumen from the proximal end thereof,
   ii) an end plate attached to a proximal end of said cannula,
   iii) means extending distally from said end plate and parallel to said cannula for engaging said carriage.

7. A drainage catheter as recited in claim 6 wherein said engaging means and said carriage include means for forming a releasable connection therebetween.

* * * * *